(12) United States Patent
Smail et al.

(10) Patent No.: US 10,710,791 B2
(45) Date of Patent: *Jul. 14, 2020

(54) HAIR TREATMENT PROCESS THAT PROVIDES SHEEN USING AN AEROSOL DEVICE

(71) Applicant: L'OREAL, Paris (FR)

(72) Inventors: Nadia Smail, Vernouillet (FR); Lionel Aubert, Asnieres sur Oise (FR); Nicolas Albisetti, Saint Gratien (FR)

(73) Assignee: L'OREAL, Paris (FR)

( * ) Notice: Subject to any disclaimer, the term of this patent is extended or adjusted under 35 U.S.C. 154(b) by 393 days.

This patent is subject to a terminal disclaimer.

(21) Appl. No.: 15/541,743

(22) PCT Filed: Jan. 8, 2016

(86) PCT No.: PCT/EP2016/050300
§ 371 (c)(1),
(2) Date: Jul. 6, 2017

(87) PCT Pub. No.: WO2016/110579
PCT Pub. Date: Jul. 14, 2016

(65) Prior Publication Data
US 2017/0362014 A1 Dec. 21, 2017

(30) Foreign Application Priority Data
Jan. 8, 2015 (FR) ...................................... 15 50164

(51) Int. Cl.
*B65D 83/20* (2006.01)
*A61K 8/31* (2006.01)
(Continued)

(52) U.S. Cl.
CPC ........... *B65D 83/205* (2013.01); *A45D 19/00* (2013.01); *A45D 19/02* (2013.01); *A45D 34/04* (2013.01);
(Continued)

(58) Field of Classification Search
CPC .... B65D 83/205; B65D 83/752; B65D 83/30; B05B 1/06; A61Q 5/12; A61Q 5/06;
(Continued)

(56) References Cited

U.S. PATENT DOCUMENTS 2,047,398 A 7/1936 Voss et al.
2,102,113 A 12/1937 Djordjevitch
(Continued)

FOREIGN PATENT DOCUMENTS

DE 2330956 A1 1/1974
DE 10 2005 025 016 A1 12/2005
(Continued)

OTHER PUBLICATIONS

Non-Final Office Action for co-pending U.S. Appl. No. 14/888,013, dated Mar. 14, 2019.
(Continued)

*Primary Examiner* — Aradhana Sasan
(74) *Attorney, Agent, or Firm* — The Marbury Law Group, PLLC

(57) ABSTRACT

The invention relates to a hair treatment process comprising the application to the hair of a composition comprising at least one fatty substance using an aerosol device comprising: —a container containing the composition and one or more propellants, it being possible for the propellant(s) to be present in the composition or, in the container, separate from the composition, —a means for dispensing said composition comprising: —a body (3) that is open at its two opposite axial ends, —an engaging part (10) that is open at its two
(Continued)

US 10,710,791 B2

Page 2 opposite axial ends, at least partially defining a dispensing orifice (12).

20 Claims, 6 Drawing Sheets

(51) Int. Cl.
　　A61K 8/37　　　(2006.01)
　　A61Q 5/06　　　(2006.01)
　　A61Q 5/12　　　(2006.01)
　　A61K 8/04　　　(2006.01)
　　A45D 34/04　　(2006.01)
　　A61K 8/92　　　(2006.01)
　　A45D 19/00　　(2006.01)
　　A45D 19/02　　(2006.01)
　　B05B 1/06　　　(2006.01)
　　A61K 8/34　　　(2006.01)
　　A61K 8/891　　(2006.01)
　　B65D 83/30　　(2006.01)
　　B65D 83/14　　(2006.01)

(52) U.S. Cl.
　　CPC .............. A61K 8/046 (2013.01); A61K 8/31
　　(2013.01); A61K 8/342 (2013.01); A61K 8/37
　　(2013.01); A61K 8/891 (2013.01); A61K 8/92
　　(2013.01); A61Q 5/06 (2013.01); A61Q 5/12
　　(2013.01); B05B 1/06 (2013.01); B65D 83/30
　　(2013.01); B65D 83/752 (2013.01); A45D
　　2019/0058 (2013.01); A61K 2800/87 (2013.01)

(58) Field of Classification Search
　　CPC ........ A61K 8/37; A61K 8/31; A61K 2800/87;
　　　　　A61K 8/92; A61K 8/891; A61K 8/342;
　　　　　A61K 8/046; A45D 2019/0058; A45D
　　　　　　　　19/02; A45D 19/00; A45D 34/04
　　See application file for complete search history.

(56) References Cited

U.S. PATENT DOCUMENTS

| 2,723,248 | A | 11/1955 | Wright |
| 3,161,460 | A | 12/1964 | Huber |
| 3,504,862 | A | 4/1970 | Lowry |
| 3,579,629 | A | 5/1971 | Pasero et al. |
| 3,589,978 | A | 6/1971 | Kamal et al. |
| 3,628,733 | A | 12/1971 | Kahn |
| 3,716,633 | A | 2/1973 | Viout et al. |
| 3,767,125 | A | 10/1973 | Gehres et al. |
| 3,792,068 | A | 2/1974 | Luedders et al. |
| 3,810,977 | A | 5/1974 | Levine et al. |
| 3,836,537 | A | 9/1974 | Boerwinkle et al. |
| 3,910,862 | A | 10/1975 | Barabas et al. |
| 3,925,542 | A | 12/1975 | Viout et al. |
| 3,946,749 | A | 3/1976 | Papantoniou |
| 3,966,403 | A | 6/1976 | Papantoniou et al. |
| 3,966,404 | A | 6/1976 | Papantoniou et al. |
| 3,990,459 | A | 11/1976 | Papantoniou |
| 4,031,307 | A | 6/1977 | DeMartino et al. |
| 4,128,631 | A | 12/1978 | Lundmark et al. |
| 4,129,711 | A | 12/1978 | Viout et al. |
| 4,131,576 | A | 12/1978 | Iovine et al. |
| 4,137,208 | A | 1/1979 | Elliott |
| 4,165,367 | A | 8/1979 | Chakrabarti |
| 4,223,009 | A | 9/1980 | Chakrabarti |
| 4,282,203 | A | 8/1981 | Jacquet et al. |
| 4,289,752 | A | 9/1981 | Mahieu et al. |
| 4,401,271 | A | 8/1983 | Hansen |
| 4,450,151 | A | 5/1984 | Shinozawa |
| 4,557,916 | A | 12/1985 | Witham |
| 4,605,553 | A | 8/1986 | Passalacqua |
| 4,693,925 | A | 9/1987 | Cheung et al. |
| 4,728,571 | A | 3/1988 | Clemens et al. |
| 4,822,596 | A | 4/1989 | Callingham et al. |
| 4,871,529 | A | 10/1989 | Sramek |
| 4,874,554 | A | 10/1989 | Lange et al. |
| 4,957,732 | A | 9/1990 | Grollier et al. |
| 4,972,037 | A | 11/1990 | Garbe et al. |
| 4,983,377 | A | 1/1991 | Murphy et al. |
| 5,297,739 | A | 3/1994 | Allen |
| 5,300,284 | A | 4/1994 | Wiechers et al. |
| 5,508,259 | A | 4/1996 | Holzner et al. |
| 5,538,717 | A | 7/1996 | La Poterie |
| 5,614,173 | A | 3/1997 | Ulmer et al. |
| 5,643,557 | A | 7/1997 | Eteve et al. |
| 5,879,669 | A | 3/1999 | Clausen et al. |
| 6,106,813 | A | 8/2000 | Mondet et al. |
| 6,166,093 | A | 12/2000 | Mougin et al. |
| 6,210,689 | B1 | 4/2001 | Martino et al. |
| 6,245,324 | B1 | 6/2001 | Hough et al. |
| 6,319,959 | B1 | 11/2001 | Mougin et al. |
| 6,350,434 | B1 | 2/2002 | Bhatt et al. |
| 6,372,876 | B1 | 4/2002 | Kim et al. |
| 6,395,265 | B1 | 5/2002 | Mougin et al. |
| 6,592,854 | B1 | 7/2003 | Dupuis |
| 6,751,886 | B2 | 6/2004 | Chang et al. |
| 7,063,834 | B2 | 6/2006 | Mougin et al. |
| 7,585,824 | B2 | 9/2009 | Popplewell et al. |
| 2002/0031478 | A1 | 3/2002 | Keller et al. |
| 2002/0150546 | A1 | 10/2002 | Mougin et al. |
| 2003/0150624 | A1 | 8/2003 | Rummel |
| 2003/0163878 | A1 | 9/2003 | Pruche |
| 2003/0185777 | A1 | 10/2003 | Banowski et al. |
| 2003/0191271 | A1 | 10/2003 | Mondet et al. |
| 2004/0047812 | A1 | 3/2004 | Pataut et al. |
| 2004/0170575 | A1 | 9/2004 | Belli et al. |
| 2004/0175404 | A1 | 9/2004 | Shefer et al. |
| 2005/0163737 | A1 | 7/2005 | Lemoine et al. |
| 2005/0220723 | A1 | 10/2005 | Benabdillah et al. |
| 2008/0019928 | A1 | 1/2008 | Franzke et al. |
| 2008/0172807 | A1 | 7/2008 | Brun |
| 2008/0274071 | A1 | 11/2008 | Kaplan et al. |
| 2009/0061004 | A1 | 3/2009 | Birkel et al. |
| 2010/0040572 | A1 | 2/2010 | Mougin |
| 2012/0097180 | A1 | 4/2012 | Harris et al. |
| 2012/0171264 | A1 | 7/2012 | Bernet et al. |
| 2012/0282190 | A1 | 11/2012 | Hammer |
| 2013/0289080 | A1 | 10/2013 | Masse et al. |
| 2013/0340786 | A1* | 12/2013 | Rodrigues .............. A61K 8/046 132/210 |
| 2014/0030196 | A1 | 1/2014 | Russell et al. |
| 2014/0079747 | A1 | 3/2014 | Dihora et al. |
| 2015/0014443 | A1 | 1/2015 | Albisetti |
| 2015/0041559 | A1 | 2/2015 | Albisetti |
| 2015/0104397 | A1 | 4/2015 | Smail et al. |
| 2015/0139917 | A1 | 5/2015 | Gawtrey et al. |
| 2016/0106634 | A1 | 4/2016 | Gawtrey et al. |
| 2018/0000700 | A1* | 1/2018 | Smail .................... A45D 34/00 |
| 2018/0016087 | A1 | 1/2018 | Smail et al. |

FOREIGN PATENT DOCUMENTS

| DE | 102008035013 | A1 | 1/2010 |
| EP | 0080976 | A1 | 6/1983 |
| EP | 0095238 | A2 | 11/1983 |
| EP | 0186507 | A2 | 7/1986 |
| EP | 0342834 | A2 | 11/1989 |
| EP | 0412704 | A2 | 2/1991 |
| EP | 0412707 | A1 | 2/1991 |
| EP | 0530974 | A1 | 3/1993 |
| EP | 0582152 | A2 | 2/1994 |
| EP | 0619111 | A1 | 10/1994 |
| EP | 0637600 | A1 | 2/1995 |
| EP | 0648485 | A1 | 4/1995 |
| EP | 0751162 | A1 | 1/1997 |
| EP | 0 974 332 | A1 | 1/2000 |
| EP | 1026220 | A1 | 8/2000 |
| EP | 1407754 | A1 | 4/2004 |
| EP | 2444160 | A1 | 4/2012 |
| EP | 2777770 | A1 | 9/2014 |
| FR | 1222944 | A | 6/1960 |

(56) References Cited

FOREIGN PATENT DOCUMENTS

| | | |
|---|---|---|
| FR | 1400366 A | 5/1965 |
| FR | 1564110 A | 3/1968 |
| FR | 1578989 A | 8/1969 |
| FR | 1580545 A | 9/1969 |
| FR | 1600138 A | 7/1970 |
| FR | 2077143 A | 10/1971 |
| FR | 2198719 A1 | 4/1974 |
| FR | 2265781 A1 | 10/1975 |
| FR | 2265782 A1 | 10/1975 |
| FR | 2350384 A1 | 12/1977 |
| FR | 2357241 A2 | 2/1978 |
| FR | 2393573 A1 | 1/1979 |
| FR | 2434194 A1 | 3/1980 |
| FR | 2439798 A1 | 5/1980 |
| FR | 2589476 A1 | 5/1987 |
| FR | 2715841 A1 | 8/1995 |
| FR | 2743297 A1 | 7/1997 |
| FR | 2814943 A1 | 4/2002 |
| FR | 2924341 A1 | 6/2009 |
| FR | 2980125 A1 | 3/2013 |
| FR | 2985201 A1 | 7/2013 |
| FR | 2985202 A1 | 7/2013 |
| FR | 2990131 A1 | 11/2013 |
| FR | 2990133 A1 | 11/2013 |
| FR | 3004929 A1 | 10/2014 |
| GB | 839805 A | 6/1960 |
| GB | 922457 A | 4/1963 |
| GB | 1021400 A | 3/1966 |
| GB | 1218222 A | 1/1971 |
| GB | 1235908 A | 6/1971 |
| GB | 1331819 A | 9/1973 |
| GB | 1408388 A | 10/1975 |
| GB | 1572626 A | 7/1980 |
| JP | 2011-213619 A | 10/2011 |
| LU | 75370 A1 | 2/1978 |
| LU | 75371 A1 | 2/1978 |
| WO | 93/23009 A1 | 11/1993 |
| WO | 94/03510 A1 | 2/1994 |
| WO | 95/00578 A1 | 1/1995 |
| WO | 98/43599 A1 | 10/1998 |
| WO | 02/078653 A1 | 10/2002 |
| WO | 02/096379 A1 | 12/2002 |
| WO | 03/049711 A2 | 6/2003 |
| WO | 2004/043608 A1 | 5/2004 |
| WO | 2011/019539 A2 | 2/2011 |
| WO | 2011/056625 A1 | 5/2011 |
| WO | 2012/035053 A1 | 3/2012 |
| WO | 2012/080255 A2 | 6/2012 |
| WO | 2013/064918 A1 | 5/2013 |
| WO | 2013/167530 A2 | 11/2013 |
| WO | 2013/167536 A2 | 11/2013 |
| WO | 2014/177646 A2 | 11/2014 |
| WO | 2014/177647 A1 | 11/2014 |
| WO | 2014/177649 A1 | 11/2014 |
| WO | 2016/001190 A1 | 1/2016 |
| WO | 2016/005703 A1 | 1/2016 |
| WO | 2016/066729 A1 | 5/2016 |
| WO | 2016/066730 A1 | 5/2016 |
| WO | 2016/110575 A1 | 7/2016 |
| WO | 2016/110578 A1 | 7/2016 |

OTHER PUBLICATIONS

Mintel: "Clean Freak Refreshing Dry Shampoo," XP007923188, Demert Brands, Mar. 2014.
Final Office Action for co-pending U.S. Appl. No. 14/399,764, dated Jun. 7, 2019.
International Search Report for counterpart PCT/EP2013/059382, dated Jun. 20, 2014.
International Search Report for counterpart PCT/EP2013/059393, dated Jun. 20, 2014.
Bezard et al., "Triglycerides of Coconut Oil," Journal of American Oil Society, 48, 3, Mar. 1971, pp. 134-139.
Oscar Blandi, http://www.skinstore.com/p-6885-oscar-blandi-pronto-dry-shampoo-spray.aspx. Published Jun. 13, 2011.
Database WPI Week 201172, Thomas Scientific, London, GB, AN 2011-N36295, XP002690571 (Jan. 25, 2013).
Mintel: "72h Anti-Perspirant Deodorant," XP007923192, Jan. 2014.
Mintel: "Brown Hair Powder Shampoo," Jun. 2011.
Mintel: "Code 10 Hair Styling Cream," XP007923186, Sep. 2001.
Mintel: "Dry Shampoo," XP007923191, Jan. 2014.
Mintel: "Foot Deodorant Spray," XP007923193, Oct. 2013.
Mintel: "One More Day Dry Shampoo," XP 007923187, Aug. 2013.
Mintel: "Refresh Dry Shampoo," Apr. 2010.
Oxford Dictionary, Half-Ester, http://www.oxfordreference.com/view/10.1093/acref/9780198529170.001.0001/acref-9780198529170-e-8589, retrieved online on Oct. 19, 2017 (Year:2017).
Todd, Charles, et al., "Volatile Silicone Fluids for Cosmetic Formulations," Cosmetics and Toiletries, vol. 91, Jan. 1976, pp. 29-32.
Non-Final Office Action for copending U.S. Appl. No. 14/399,753, dated Sep. 8, 2015.
Final Office Action for copending U.S. Appl. No. 14/399,753, dated Mar. 30, 2016.
Non-Final Office Action for copending U.S. Appl. No. 14/399,764, dated Dec. 17, 2015.
International Search Report for counterpart PCT/EP2014/058896, dated Sep. 23, 2014.
International Search Report and Written Opinion for counterpart PCT/EP2014/058892, dated Oct. 29, 2014.
International Search Report for counterpart PCT/EP2014/058894, dated Sep. 29, 2014.
Final Office Action for copending U.S. Appl. No. 13/993,413, dated Nov. 14, 2016.
Final Office Action for copending U.S. Appl. No. 14/399,764, dated Aug. 5, 2016.
Non-Final Office Action for copending U.S. Appl. No. 14/888,002, dated Sep. 9, 2016.
Non-Final Office Action for copending U.S. Appl. No. 14/787,983, dated Sep. 15, 2016.
Final Office Action for copending U.S. Appl. No. 14/399,753, dated Sep. 30, 2016.
Non-Final Office Action for copending U.S. Appl. No. 14/888,013, dated Apr. 13, 2017.
Non-Final Office Action for copending U.S. Appl. No. 14/399,764, dated Mar. 8, 2017.
Final Office Action for copending U.S. Appl. No. 14/787,983, dated May 30, 2017.
International Search Report for counterpart PCT/FR2015/051896, dated Oct. 19, 2015.
International Search Report for counterpart PCT/EP2015/075061, dated Jan. 20, 2016.
International Search Report for counterpart PCT/EP2015/075062, dated Jan. 26, 2016.
Non-Final Office Action for copending U.S. Appl. No. 15/324,804, dated Mar. 5, 2018.
Non-Final Office Action for copending U.S. Appl. No. 15/523,232, dated Feb. 23, 2018.
Non-Final Office Action for copending U.S. Appl. No. 15/523,242, dated Aug. 31, 2017.
Final Office Action for copending U.S. Appl. No. 14/888,013, dated Aug. 15, 2017.
Final Office Action for copending U.S. Appl. No. 14/888,002, dated Sep. 21, 2017.
Final Office Action for copending U.S. Appl. No. 14/399,764, dated Aug. 16, 2017.
Non-Final Office Action for copending U.S. Appl. No. 14/399,753, dated Oct. 4, 2017.
Non-Final Office Action for copending U.S. Appl. No. 14/787,983, dated May 11, 2018.
Non-Final Office Action for copending U.S. Appl. No. 15/523,242, dated Mar. 27, 2018.
International Search Report for counterpart Application PCT/EP2011/072617, dated Jul. 5, 2012.
Non-Final Office Action for copending U.S. Appl. No. 15/541,738, dated May 17, 2018.

(56) References Cited

OTHER PUBLICATIONS

Non-Final Office Action for copending U.S. Appl. No. 13/993,413, dated May 19, 2015.
Final Office Action for copending U.S. Appl. No. 13/993,413, dated Dec. 30, 2015.
Non-Final Office Action for copending U.S. Appl. No. 13/993,413, dated Nov. 8, 2017.
Final Office Action for copending U.S. Appl. No. 13/993,413, dated Jul. 5, 2018.
Brunauer et al., "Adsorption of Gases in Multimolecular Layers," Journal of the American Chemical Society, vol. 60, Feb. 1938, pp. 309-319.
International Search Report for PCT/EP2016/050295, dated Mar. 23, 2016.
International Search Report for PCT/EP2016/050299, dated Mar. 23, 2016.
International Search Report for PCT/EP2016/050300, dated Mar. 16, 2016.
Final Office Action for co-pending U.S. Appl. No. 14/787,983, dated Dec. 27, 2018.
Final Office Action for co-pending U.S. Appl. No. 15/532,232, dated Jan. 25, 2019.
Non-Final Office Action for co-pending U.S. Appl. No. 15/541,738, dated Feb. 5, 2019.
Non-Final Office Action for co-pending U.S. Appl. No. 15/541,741, dated Feb. 27, 2019.
International Search Report for counterpart Application No. PCT/EP2015/064780, dated Sep. 14, 2015.
Porter, M.R., "Handbook of Surfactants," published by Blackie & Son (Glasgow and London), 1991, pp. 116-178.
Mintel: "Styling Mousse," XP002736036, Nov. 2008.
Notice of Allowance for co-pending U.S. Appl. No. 15/523,242, dated Jun. 12, 2019.
Non-Final Office Action for co-pending U.S. Appl. No. 14/787,983, dated Jun. 26, 2019.
Final Office Action for co-pending U.S. Appl. No. 15/541,741, dated Jul. 11, 2019.
Notice of Allowance for co-pending U.S. Appl. No. 15/541,738, dated Sep. 4, 2019.
Supplemental Notice of Allowance for co-pending U.S. Appl. No. 15/523,242, dated Sep. 5, 2019.
Non-Final Office Action for co-pending U.S. Appl. No. 15/322,771, dated Sep. 6, 2019.
Non-Final Office Action for co-pending U.S. Appl. No. 15/324,804, dated Oct. 10, 2019.
Final Office Action for copending U.S. Appl. No. 15/324,804, dated Nov. 30, 2018.
Non-Final Office Action for copending U.S. Appl. No. 14/399,764, dated Dec. 5, 2018.
Non-Final Office Action for copending U.S. Appl. No. 15/523,242, dated Dec. 17, 2018.
Final Office Action for copending U.S. Appl. No. 15/523,232, dated Jan. 25, 2019.
Final Office Action for co-pending U.S. Appl. No. 14/888,013, dated Oct. 18, 2019.
Non-Final Office Action for co-pending U.S. Appl. No. 14/888,002, dated Oct. 7, 2019.
Non-Final Office Action for co-pending U.S. Appl. No. 15/523,232, dated Feb. 20, 2020.
Final Office Action for co-pending U.S. Appl. No. 14/787,983, dated Feb. 26, 2020.
Non-Final Office Action for co-pending U.S. Appl. No. 15/541,741, dated Mar. 3, 2020.
Clearco, "Cyclo-1400-DM D5 Cyclomethicone/dimethicone blend," ([retrieved from on-line website: http://www.clearcoproducts.com/cyclo-1400-d5-blend.html], 2013, pp. 1-2.
Wayback Machine to support publication year of Clearco (Year: 2013).
Non-Final Office Action for copending U.S. Appl. No. 15/322,771, dated Mar. 20, 2020.
Final Office Action for copending U.S. Appl. No. 15/324,804, dated Apr. 20, 2020.
Final Office Action for copending U.S. Appl. No. 14/888,002, dated Jun. 1, 2020.

\* cited by examiner

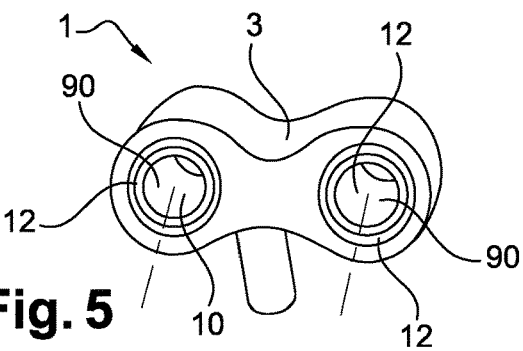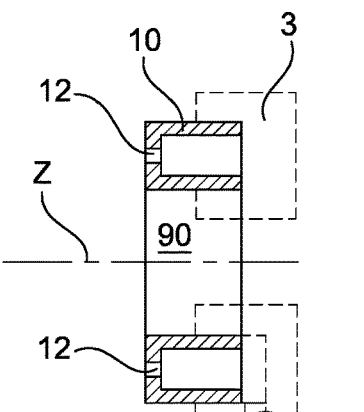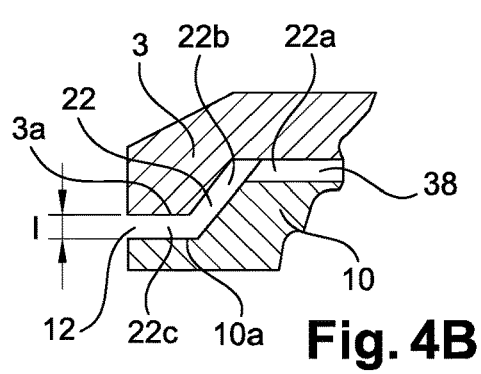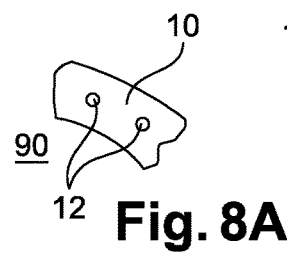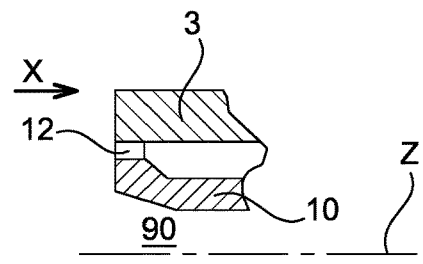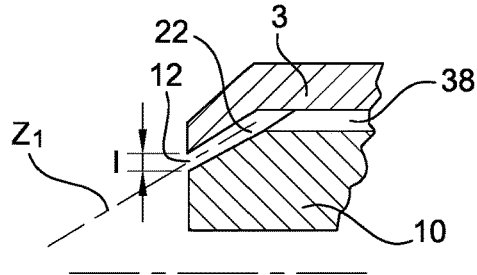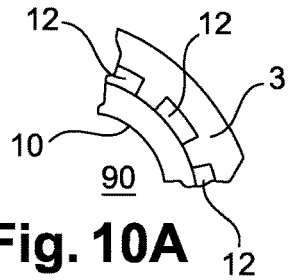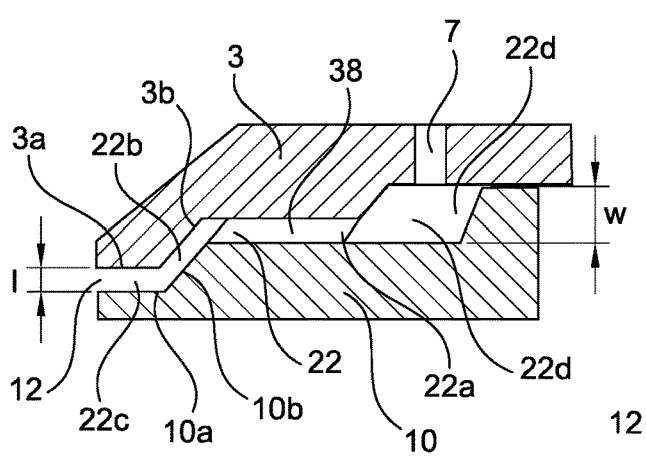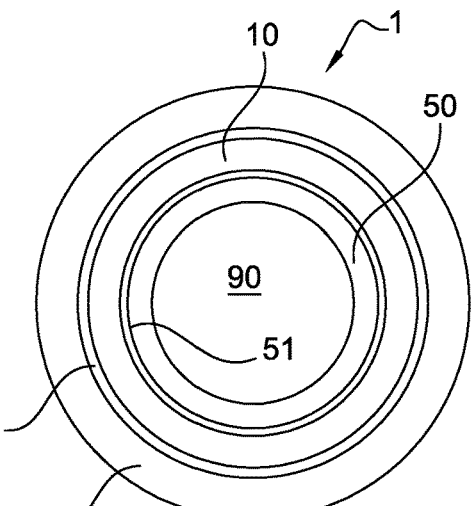

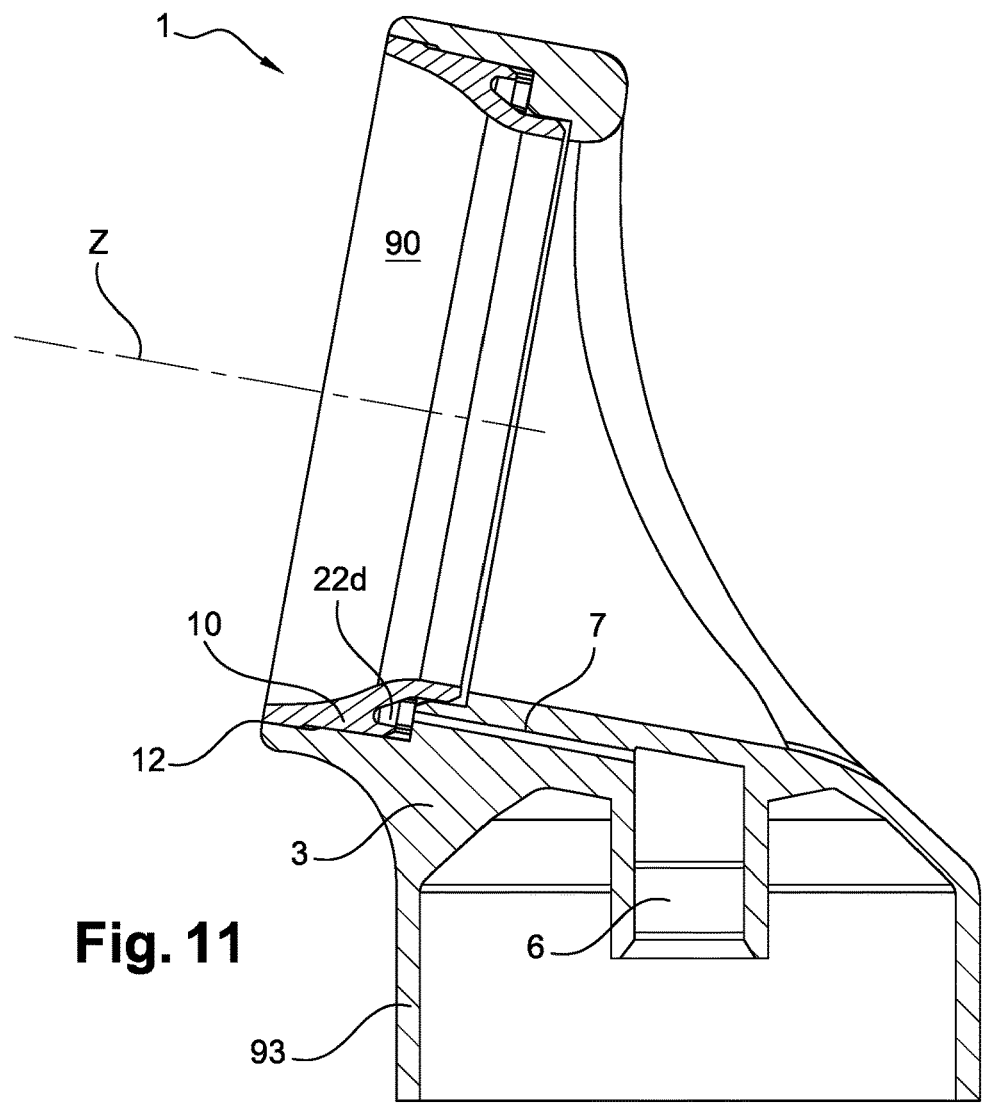
Fig. 11
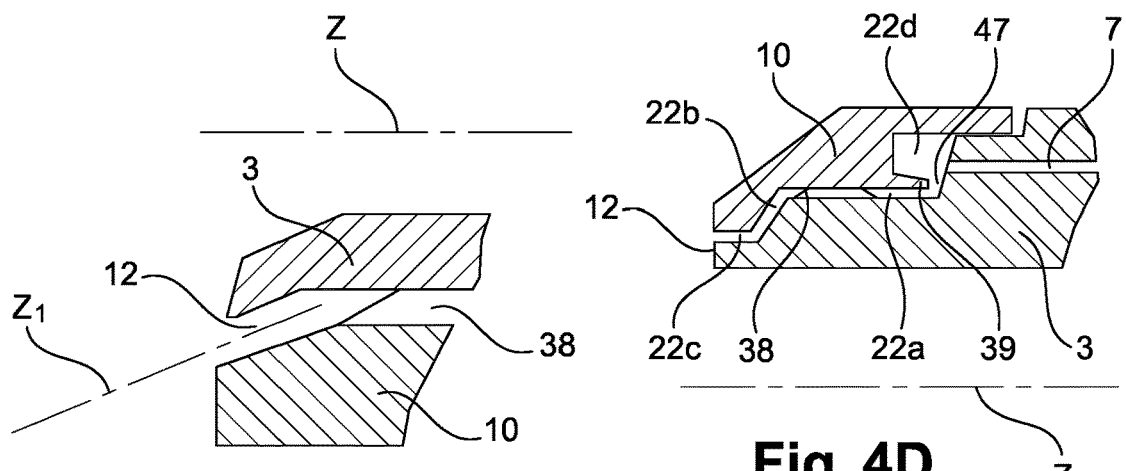
Fig. 4E
Fig. 4D

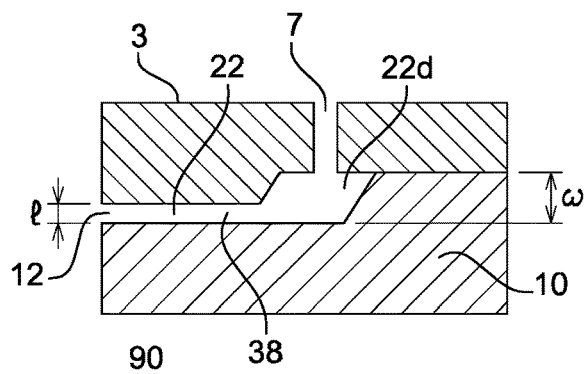
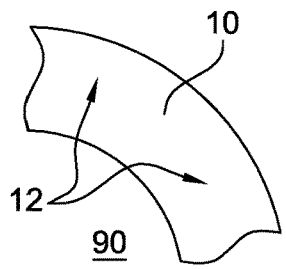
Fig. 4F            Fig. 8B
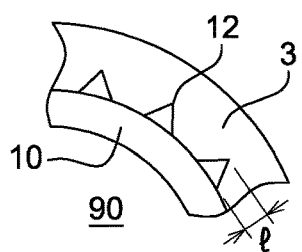    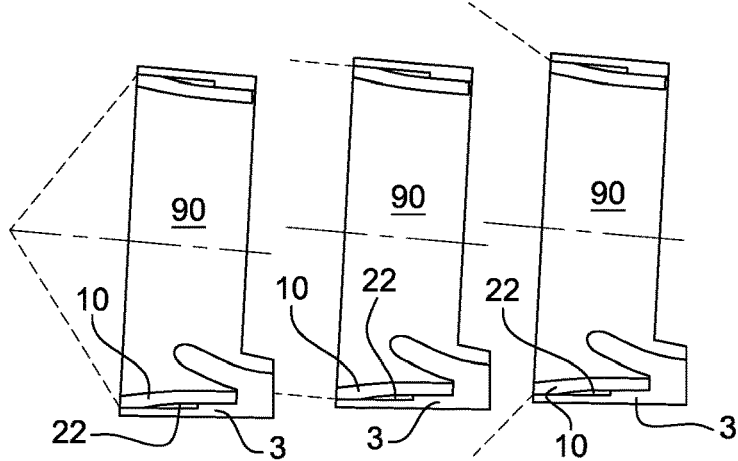
Fig. 10B      Fig. 13A  Fig. 13B  Fig. 13C
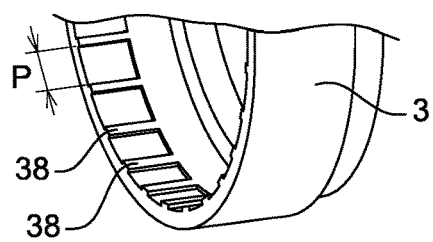
Fig. 12A
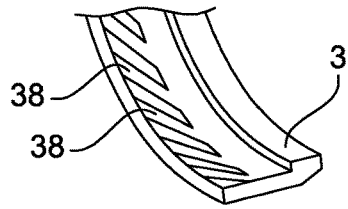      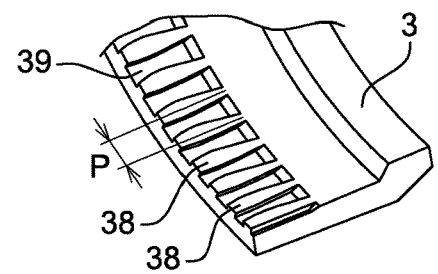
Fig. 12B          Fig. 12C

HAIR TREATMENT PROCESS THAT PROVIDES SHEEN USING AN AEROSOL DEVICE

CROSS REFERENCE TO RELATED APPLICATION

This is a national stage application of PCT/EP2016/050300, filed internationally on Jan. 8, 2016, which claims priority to French Application No. 1550164, filed on Jan. 8, 2015, both of which are hereby incorporated by reference in their entireties.

The present invention relates to a hair treatment process using a particular aerosol device comprising a composition comprising at least one fatty substance, and also relates to the particular aerosol device comprising the hair composition.

"Sheen" products that are applied as finishing care, i.e. on dried hair, exist. These products are difficult to apply since, if the amount applied is too large or poorly distributed, the head of hair generally has a greasy look and feel.

There is therefore a need for development of a new hair treatment process that can give the hair improved sheen while at the same time obtaining a natural-looking result.

The applicant has found, surprisingly and advantageously, that the use of a treatment process using a device equipped with a dispensing means comprising a body that is open at its two opposite axial ends and an engaging part that is open at its two opposite axial ends, at least partially defining a dispensing orifice, for dispensing a composition comprising at least one fatty substance makes it possible to easily and rapidly obtain a shiny, manageable and light hairstyle.

According to a first of its aspects, a subject of the invention is a hair treatment process comprising the application to the hair of a composition comprising at least one fatty substance using an aerosol device comprising:
- a container containing the composition and one or more propellants, it being possible for the propellant(s) to be present in the composition or, in the container, separate from the composition,
- a means for dispensing said composition comprising:
  - a body that is open at its two opposite axial ends,
  - an engaging part that is open at its two opposite axial ends, at least partially defining a dispensing orifice.

This particular combination allows easy application and a uniform, fine, light distribution of the hair composition on the head of hair, thus resulting in hair sheen with a natural result.

The process according to the invention thus gives the hair sheen, while conferring in particular manageability, lightness and softness on the head of hair, and a good touch.

The present invention also relates to an aerosol device comprising:
- a container containing:
  - one or more propellants, and
  - a composition comprising at least one fatty acid ester and/or fatty alcohol ester and at least one non-siliconized oil,
it being possible for the propellant(s) to be present in the composition or, in the container, separate from the composition,
- a means for dispensing said composition comprising:
  - a body that is open at its two opposite axial ends,
  - an engaging part that is open at its two opposite axial ends, at least partially defining a dispensing orifice.

A subject of the present invention is also the use of an aerosol device as defined previously for giving the hair sheen.

Other subjects, characteristics, aspects and advantages of the invention will emerge even more clearly on reading the description and the example that follows.

In that which follows and unless otherwise indicated, the limits of a range of values are included within this range, in particular in the expressions "of between" and "ranging from . . . to . . . ".

Moreover, the expression "at least one" used in the present description is equivalent to the expression "one or more".

According to the invention, the process of the invention comprises the application to the hair of a composition comprising of at least one fatty substance.

The term "fatty substance" means an organic compound that is insoluble in water at ordinary temperature (25° C.) and at atmospheric pressure (760 mmHg) (solubility of less than 5%, preferably 1% and even more preferentially 0.1%). The fatty substances have in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The fatty substances of the invention preferably do not contain any salified or non-salified carboxylic acid groups (—C(O)OH or —C(O)O—). The fatty substances of the invention are neither oxyalkylenated nor glycerolated.

The term "oil" means a "fatty substance" that is liquid at room temperature (25° C.) and at atmospheric pressure (760 mmHg).

The term "non-silicone oil" means an oil not containing any silicon atoms (Si) and the term "silicone oil" means an oil containing at least one silicon atom.

More particularly, the fatty substances are chosen from $C_6$-$C_{16}$ hydrocarbons, hydrocarbons containing more than 16 carbon atoms, non-silicone oils of animal origin, plant or synthetic oils of triglyceride type, fluoro oils, fatty alcohols, fatty acid and/or fatty alcohol esters other than triglycerides and plant waxes, non-silicone waxes and silicones.

It is recalled that, for the purposes of the invention, the fatty alcohols, esters and acids more particularly contain at least one saturated or unsaturated, linear or branched hydrocarbon-based group comprising 6 to 30 carbon atoms, which is optionally substituted, in particular by one or more hydroxyl groups (in particular 1 to 4). If they are unsaturated, these compounds may comprise one to three conjugated or unconjugated carbon-carbon double bonds.

As regards the $C_6$-$C_{16}$ hydrocarbons, they are linear, branched, and optionally cyclic, and are preferably chosen from alkanes. Examples that may be mentioned include hexane, dodecane, and isoparaffins, for instance isohexadecane and isodecane.

A hydrocarbon-based oil of animal origin that may be mentioned is perhydrosqualene.

The triglyceride oils of plant or synthetic origin are preferably chosen from liquid fatty acid triglycerides containing from 6 to 30 carbon atoms, for instance heptanoic or octanoic acid triglycerides, or alternatively, for example, sunflower oil, corn oil, soybean oil, pumpkin oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil.

The linear or branched hydrocarbons of mineral or synthetic origin, containing more than 16 carbon atoms, are preferably chosen from liquid paraffins, petroleum jelly, liquid petroleum jelly, polydecenes and hydrogenated polyisobutene such as Palream®.

The fluoro oils may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that may be used in the composition according to the invention are linear or branched, saturated or unsaturated alcohols comprising from 6 to 30 carbon atoms and more particularly from 8 to 30 carbon atoms. Examples that may be mentioned include cetyl alcohol, stearyl alcohol and the mixture thereof (cetylstearyl alcohol), octyldodecanol, 2-butyloctanol, 2-hexyldecanol, 2-undecylpentadecanol, oleyl alcohol and linoleyl alcohol.

The wax(es) that may be used in the composition according to the invention are chosen especially from carnauba wax, candelilla wax and alfalfa wax, paraffin wax, ozokerite, plant waxes such as olive wax, rice wax, hydrogenated jojoba wax or the absolute waxes of flowers such as the essential wax of blackcurrant blossom sold by the company Bertin (France), animal waxes such as beeswaxes, or modified beeswaxes (cerabellina); other waxes or waxy starting materials that may be used according to the invention are especially marine waxes such as the product sold by the company Sophim under the reference M82, and polyethylene waxes or polyolefin waxes in general.

Regarding the fatty acid and/or fatty alcohol esters, advantageously other than the triglycerides mentioned above, mention may especially be made of linear or branched, saturated or unsaturated esters of $C_1$-$C_{26}$ aliphatic mono- or polyacids and linear or branched, saturated or unsaturated esters of $C_1$-$C_{26}$ aliphatic mono- or polyalcohols, the total number of carbon atoms in the esters being more particularly greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made especially of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, use is preferably made of ethyl, isopropyl, myristyl, cetyl or stearyl palmitate, 2-ethylhexyl palmitate, 2-octyldecyl palmitate, alkyl myristates, such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

More particularly, use is made of monoesters and diesters and in particular mono- or di-oleate, -stearate, -behenate, -oleate/palmitate, -linoleate, -linolenate or -oleate/stearate of sucrose, glucose or methylglucose. Mention may be made, by way of example, of the product sold under the name Glucate® DO by the company Amerchol, which is a methylglucose dioleate.

Examples of esters or mixtures of esters of sugar and of fatty acid that may also be mentioned include:
    the products sold under the names F160, F140, F110, F90, F70 and SL40 by the company Crodesta, respectively denoting sucrose palmitate/stearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name Ryoto Sugar Esters, for example referenced B370 and corresponding to sucrose behenate formed from 20% monoester and 80% diester-triester-polyester;

the sucrose mono-dipalmitate/stearate sold by the company Goldschmidt under the name Tegosoft® PSE.

The silicones that may be used in accordance with the invention may be in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from amino groups, aryl groups and alkoxy groups.

Organopolysiloxanes are defined in greater detail in Walter Noll's *Chemistry and Technology of Silicones* (1968), Academic Press. They may be volatile or non-volatile.

These silicones are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made, in a nonlimiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes having dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The organomodified silicones that may be used in accordance with the invention are silicones as defined previously and comprising in their structure one or more organofunctional groups attached via a hydrocarbon-based group.

The organomodified silicones may be polydiarylsiloxanes, in particular polydiphenyl-siloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1\times10^{-5}$ to $5\times10^{-2}$ m$^2$/s at 25° C.

Among the polyalkylarylsiloxanes, examples that may be mentioned include the products sold under the following names:

the Silbione® oils of the 70 641 series from Rhodia;

oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Among the organomodified silicones, mention may also be made of polyorganosiloxanes comprising:

substituted or unsubstituted amino groups, such as the products sold under the names GP 4 Silicone Fluid and GP 7100 by the company Genesee or the products sold under the names Q2 8220 and Dow Corning 929 or 939 by the company Dow Corning. The substituted amino groups are, in particular, $C_1$-$C_4$ aminoalkyl groups;

alkoxy groups such as the product sold under the name Silicone Copolymer F-755 by SWS Silicones, and Abil Wax® 2428, 2434 and 2440 by the company Goldschmidt.

The fatty substances are advantageously chosen from $C_6$-$C_{16}$ hydrocarbons, hydrocarbons containing more than 16 carbon atoms, triglycerides, fatty alcohols, esters of fatty acids and/or of fatty alcohols other than triglycerides, and silicones, or mixtures thereof.

Preferably, the fatty substance(s) are chosen from liquid fatty substances, in particular from mineral oils, liquid fatty alcohols, liquid esters of fatty acids and/or of fatty alcohols, and silicone oils, or mixtures thereof.

Even more preferentially, the fatty substance(s) are chosen from mineral oils, liquid fatty alcohols, and liquid esters of fatty acids and/or of fatty alcohols, or mixtures thereof.

According to a preferred embodiment, the composition comprises at least one ester, which is preferably liquid, of fatty acids and/or of fatty alcohols, and at least one non-silicone oil.

When the propellant(s) are present in the composition, the fatty substance(s) is or are present in an amount ranging from 0.1% to 80% by weight, even better still from 2% to 60% by weight, and even more preferentially from 5% to 30% by weight, relative to the total weight of the composition.

The composition may also comprise one or more $C_2$-$C_4$ monoalcohols.

$C_2$-$C_4$ monoalcohol(s) which can be used in the aerosol device of the invention include, in particular, ethanol or isopropanol, or better still ethanol.

When they are present, the $C_2$-$C_4$ monoalcohol(s) is or are preferably present in an amount ranging from 1% to 70% by weight, even better still from 5% to 60% by weight, and even more preferentially from 10% to 50% by weight, relative to the total weight of the composition, when the propellant(s) are present in the composition.

The composition according to the invention may contain one or more additional organic solvents such as polyols, for instance glycerol, propylene glycol or polyethylene glycols.

It may also contain water.

Preferably, the composition according to the invention contains less than 5% by weight of water relative to the total weight of the composition, when the propellant(s) are present in the composition. Even more preferentially, it does not contain any added water. The composition is then said to be anhydrous.

The container of the device according to the invention also comprises one or more propellants.

Examples of propellant which can be used in the aerosol device of the present invention are liquefied gases such as dimethyl ether, 1,1-difluoroethane, or $C_3$-$C_5$ alkanes, such as propane, isopropane, n-butane, isobutane or pentane, or compressed gases such as air, nitrogen, carbon dioxide, and mixtures thereof.

Mention may be made preferably of $C_3$-$C_5$ alkanes and in particular propane, n-butane, isobutane and mixtures thereof.

The agent(s) may be present in the composition or, as a variant, in the container containing the composition, but separate from the composition.

The agent(s) are preferably present in the composition.

When the propellant(s) are present in the composition, it (they) is (are) preferably present in an amount ranging from 10% to 90% by weight, even better still from 15% to 80% by weight and even more preferentially from 20% to 75% by weight relative to the total weight of the composition.

The compositions defined in the invention may further comprise one or more additives chosen from anionic, cationic, nonionic, amphoteric or zwitterionic, conditioning or fixing polymers, fragrances, dyes, UV-protective screening agents, acids, bases, nacres and flakes.

These additives may be present in the composition according to the invention in an amount ranging from 0% to 20% by weight, relative to the total weight of the composition, when the propellant(s) are present in the composition.

Those skilled in the art will take care to choose these optional additives and their amounts so that they do not harm the properties of the compositions of the present invention.

The compositions in accordance with the invention are packaged in an aerosol device comprising a container, also known as a reservoir.

The container is pressurized and comprises the composition to be dispensed. The container containing the pressurized composition may be opaque or transparent. It may be made of glass, of polymer or of metal, optionally coated with a protective varnish coat.

As already mentioned previously, the container contains both the propellant(s) and the other ingredients of the composition, in a single compartment, or as a variant in two compartments. According to the latter variant, the container may be constituted of an outer aerosol can comprising an inner bag hermetically welded to a valve. The various ingredients of the composition are introduced into the inner bag and a propellant is introduced between the bag and the can at a sufficient pressure to make the product come out in the form of a spray.

The container is equipped at its top end with a valve that seals the system.

Onto this valve is fitted a dispensing means, on which the user can press to make the product come out. This dispensing means is also known as a diffuser.

As indicated above, the dispensing means according to the invention comprises a body that is open at its two opposite axial ends and an engaging part that is open at its two opposite axial ends, at least partially defining at least one dispensing orifice.

In particular, the dispensing orifice is preferably defined between the body and the engaging part but may, alternatively, be defined entirely by the engaging part.

By virtue of the device of the invention, a passage is formed through the dispensing means and more particularly through the body and the engaging part, allowing a flow of air to be established through the dispensing means when the product to be dispensed is emitted, and this can prove advantageous when the product is emitted in the form of a spray, allowing a current of air to be created through the dispensing means in order to accompany the flow of the spray.

Moreover, the passage through the dispensing means can be produced with dimensions sufficient to allow, if desired, a finger or a lock of hair to be inserted into this passage. This can make it easier to apply a product to the finger or the lock of hair.

If desired, the invention can also make it easier to produce a dispensing orifice having an annular cross section between the engaging part and the body, allowing the formation of a hollow spray. Alternatively, a plurality of dispensing orifices are formed between the body and the engaging part, for example in order to dispense the product in the form of a number of sprays or jets. The number of dispensing orifices can in particular be between, limits included, 2 and 80 preferably between 5 and 60. It may for example be equal to 10. The dispensing orifices each have for example a cross section greater than or equal to 0.0025 $mm^2$, better still 0.006 $mm^2$ and are preferably spaced apart from one another (measurement along a straight line between the centres of mass of the orifices) by a distance of more than 1 mm.

In another variant, several dispensing orifices are formed entirely in the engaging part. The orifices may be constructed in such a way that the jet exiting from each orifice swirls, especially by virtue of at least two swirl ducts oriented tangentially around the axis of the orifice. The engaging part may have a U-shaped axial half-section. The body may have two concentric mounting skirts between which the engaging part is fastened. The body may comprise a crown into which the engaging part is inserted, the crown possibly bearing one or more reliefs defining, with the engaging part, ducts, especially swirl ducts, for supplying the dispensing orifice.

The body may define a housing that receives the engaging part, which is then called a core.

The dispensing orifice(s) may be open at rest. The expression "at rest" should be understood as meaning before the engaging part is exposed to the pressure of the product to be dispensed. Thus, in this case, the dispensing orifice(s) are already formed and open when the product is sent into the dispensing means in order to be dispensed. Alternatively, the dispensing orifice is formed at the time the product is dispensed, by virtue for example of the elasticity of at least a portion of the body or of the engaging part, which deforms under the pressure of the product at the time it is dispensed.

By virtue of the invention, in the case of spraying, the spray can be emitted at a relatively high flow rate, if desired, while having a dispensing means which has a relatively simple design and functions reliably. In particular, the dispensing orifice may be produced with well-defined dimensions. In addition, the dispensing means may be aesthetically pleasing to the consumer.

The body may have a first surface that flares towards the outside, or converges towards the outside, and the engaging part may have a second surface, opposite the first surface, that diverges towards the outside, or converges towards the outside. The first surface may be conical. The second surface may be conical, with the same angle as the first surface or with a greater or smaller angle.

A different angle that results in a narrowing of the space may lead to an acceleration of the jet before it exits, and this may be advantageous in the context of a spray.

There may be one or more than one dispensing orifice and it may have an annular shape or some other shape. The dispensing orifice may have, in the circumferential direction, a constant width. The one or more dispensing orifices may be defined between two concentric surfaces of revolution, for example in the form of cylinders of revolution.

The dispensing orifice(s) may have axial symmetry, preferably rotational symmetry, in particular around the dispensing axis. The dispensing axis is defined by the general direction in which the product is dispensed by the dispensing means.

When the dispensing means comprises several dispensing orifices, they preferably have the following characteristics.

Their cross section is advantageously a disc.

They are preferably cylindrical in shape or approximately cylindrical in shape.

The depth of each orifice is advantageously between 0.5 and 2 mm. A long length makes it possible to create an individual spray with a reduced cone so as to create a tubular effect with a sizeable number of orifices. A short length allows a very wide individual spray and even further enlarges the application surface of the multi-orifice diffuser.

The sum of the cross sections of the orifices in the ring is preferably chosen to be close to the surface area of the orifice in the nozzle.

With the same valve, it is possible to obtain various types of spray by choosing the number and the cross section of the orifices. Use may, for example, be made of a dispensing means according to the invention equipped with 80 orifices of 0.005 $mm^2$ so as to obtain a gentle mist or a dispensing means according to the invention equipped with 10 orifices of 0.1 $mm^2$ so as to obtain a powerful spray.

The orifices may be distributed in various ways. They may be equidistant on the periphery of the ring, equidistant from one another on a portion of the ring, or distributed in equidistant groups composed of several equidistant orifices.

It is possible to create a ring fully supporting the dispensing orifices which may be cylindrical. In this configuration, it is possible to produce small swirl orifices with a different design from the internal and external rings so as to allow the creation of a ring intended to create the "centre post" function at the rear.

The engaging part is preferably attached, thereby making it, and the body, easier to manufacture. Alternatively, the engaging part is moulded in one piece with the body, in particular in the case of the dispensing of a foam, it then being possible for the dispensing orifice to have a larger cross section than in the case of the spraying of a spray.

The space formed between the body and the engaging part is supplied by at least one supply duct, the section of which is preferably greater than that of the dispensing orifice, thereby making it easier to fill this space before the product emerges through the dispensing orifice.

A product dispensing chamber may advantageously be formed, between the engaging part and the body, upstream of the dispensing orifice. This can make the emission of a homogeneous spray, in particular, easier.

The supply duct for the product may open into this chamber, which preferably has an annular shape. Its width, which corresponds to the gap between the engaging part and the body, is preferably greater than the maximum width of the passage, via which the dispensing chamber communicates with the dispensing orifice.

At least one of the body and the engaging part, preferably the body, may have at least one relief for centring the engaging part in relation to the body, and preferably at least ten, better still at least twenty, and even better still at least forty reliefs. These reliefs may extend as far as the edge of the part in which they are produced so as to generate a multitude of orifices via which jets of product exit, the centring reliefs being oriented in particular parallel to the dispensing axis or obliquely in the same circumferential direction around the axis, and optionally also being able to define, between one another, sectional narrowings that cause the jet of product to be accelerated. This or these reliefs are preferably located set back from the dispensing orifice when it is desired to generate a spray in the form of a single jet. The reliefs can be produced on the body, being for example in the form of axial ribs that are distributed regularly around the entire surface of the body opposite the engaging part.

The centring reliefs may optionally ensure alone that the engaging part is held on the body. Alternatively, the engaging part is fixed to the body somewhere other than in the region of the centring reliefs, it being possible in this case for the centring reliefs to have or not have a function of holding the engaging part on the body.

Preferably, the engaging part is fixed in relation to the body. Alternatively, the engaging part is fixed in an adjustable manner in relation to the body, in order for example to allow the user to adjust the width of the dispensing orifice or to close the latter when not in use, for example by screwing it through a quarter turn, this screwing being accompanied by an axial movement of the engaging part in relation to the body.

The engaging part may be flush with the front end of the body so as to generate a spray with an axis substantially parallel to the axis of the engaging part.

The engaging part may extend axially beyond the front end of the body by an amount between 0.01 and 1 mm, better still between 0.01 and 0.5 mm. The spray may then diverge towards the axis of the engaging part.

The engaging part may be axially set back from the front end of the body by an amount between 0.01 and 1 mm, better still between 0.01 and 0.5 mm. The spray may then converge towards the axis of the engaging part.

The invention makes it possible to easily produce, if desired, a dispensing orifice having a circular internal contour. The inside diameter of the passage formed through the dispensing means is for example greater than or equal to 10 mm, better still greater than or equal to 15 mm, 20 mm or 30 mm. When the passage does not have a circular section, the "inside diameter" denotes the diameter of the largest circle inscribed in this passage.

The dispensing means may comprise at least two housings and two engaging parts that are disposed in the housings and each define with the body, at rest, a dispensing orifice according to the invention. The dispensing axes may then be parallel or not parallel, intersecting or not intersecting, for example may converge towards one another.

The dispensing orifice may have, in axial half-section, an axis that converges or diverges in relation to the spraying direction.

The invention also relates to an aerosol device comprising:
  a container containing:
    one or more propellants, and
    a composition comprising one or more sebum-absorbing powders with a sebum uptake of greater than or equal to 35 ml/100 g,
  it being possible for the propellant(s) to be present in the composition or, in the container, separate from the composition,
  a means for dispensing said composition comprising:
    a body,
    an engaging part, in particular a core, defining with the body, at rest, at least one dispensing orifice having an annular cross section.

The invention also relates to an aerosol device comprising:
  a container comprising a valve rod or pump rod, containing:
    one or more propellants, and a composition comprising one or more sebum-absorbing powders with a sebum uptake of greater than or equal to 35 ml/100 g, it being possible for the propellant(s) to be present in the composition or, in the container, separate from the composition, a means for dispensing said composition comprising:
a body provided with an end piece for connecting to the valve rod or pump rod,
a part attached to the body, at least partially defining at least one dispensing orifice having in particular an annular cross section at rest or several dispensing orifices distributed around a dispensing axis (Z), the dispensing means not being a through-dispensing means along the dispensing axis (Z), the body being closed along the dispensing axis (Z) and said part being in particular of annular shape, or the body having a through-opening along the dispensing axis (Z) and said part closing this opening.

BRIEF DESCRIPTION OF THE DRAWINGS

The invention may be better understood from reading the following detailed description of non-limiting illustrative embodiments thereof and from examining the appended drawing, in which:

FIGS. 4A to 4F illustrate various arrangements, among others, of the engaging part and the body, FIG. 5 illustrates the possibility of producing the dispensing means with two dispensing orifices according to the invention, FIG. 6 shows a front view of a dispensing means having concentric dispensing orifices, FIG. 7 is an axial section through a variant embodiment of the engaging part, FIGS. 8A and 8B are partial front views of different examples of configurations of the engaging part from FIG. 7, FIG. 9 is a partial axial section through a variant embodiment of the dispensing orifice, FIGS. 10A and 10B are front views along X of different examples of configurations according to FIG. 9, FIG. 11 is a view similar to FIG. 2 of a variant embodiment of the dispensing means, FIGS. 12A to 12C illustrate various examples of arrangements of the reliefs on the body, FIGS. 13A to 13C illustrate various examples of configurations of the engaging part with respect to the body.

Figure 1:
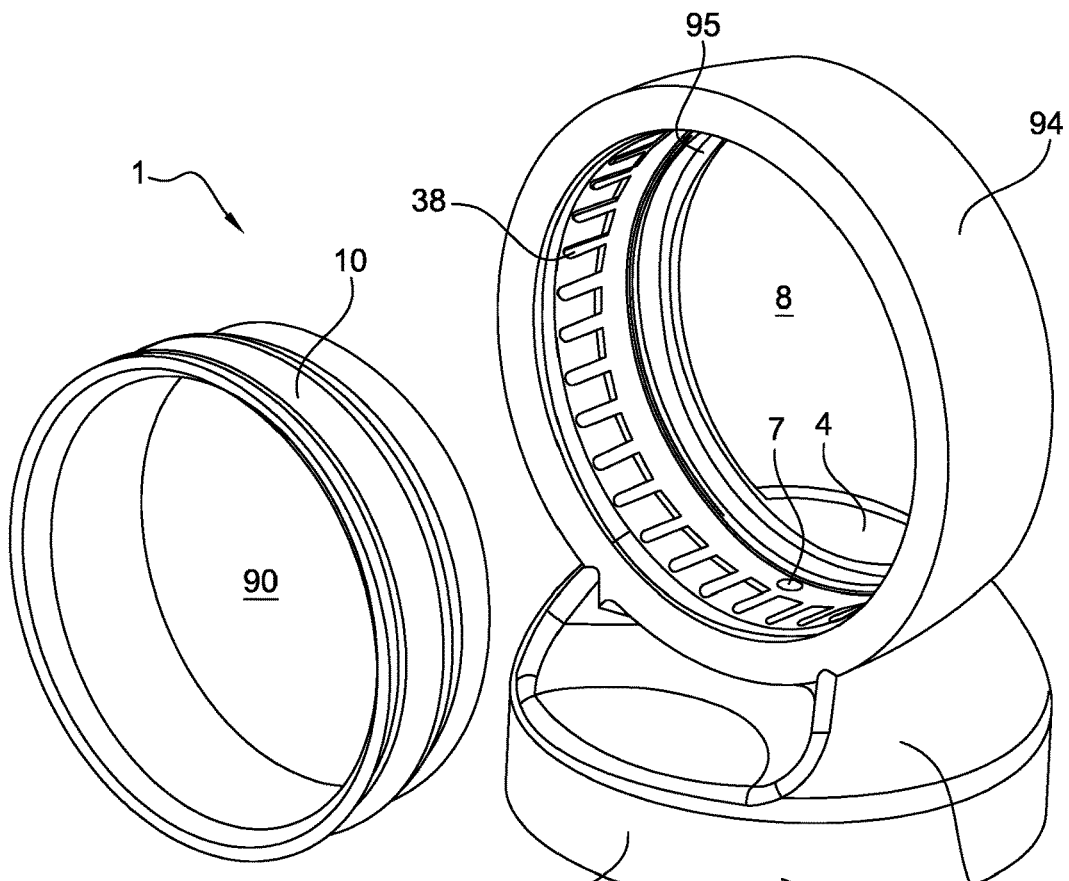
FIG. 1 schematically shows a perspective view of an example of a dispensing means produced in accordance with the invention, before the engaging part is fitted on the body of the dispensing means.

In the drawing, the actual respective proportions of the various constituent elements have not always been respected, for the sake of clarity.

Figure 2:
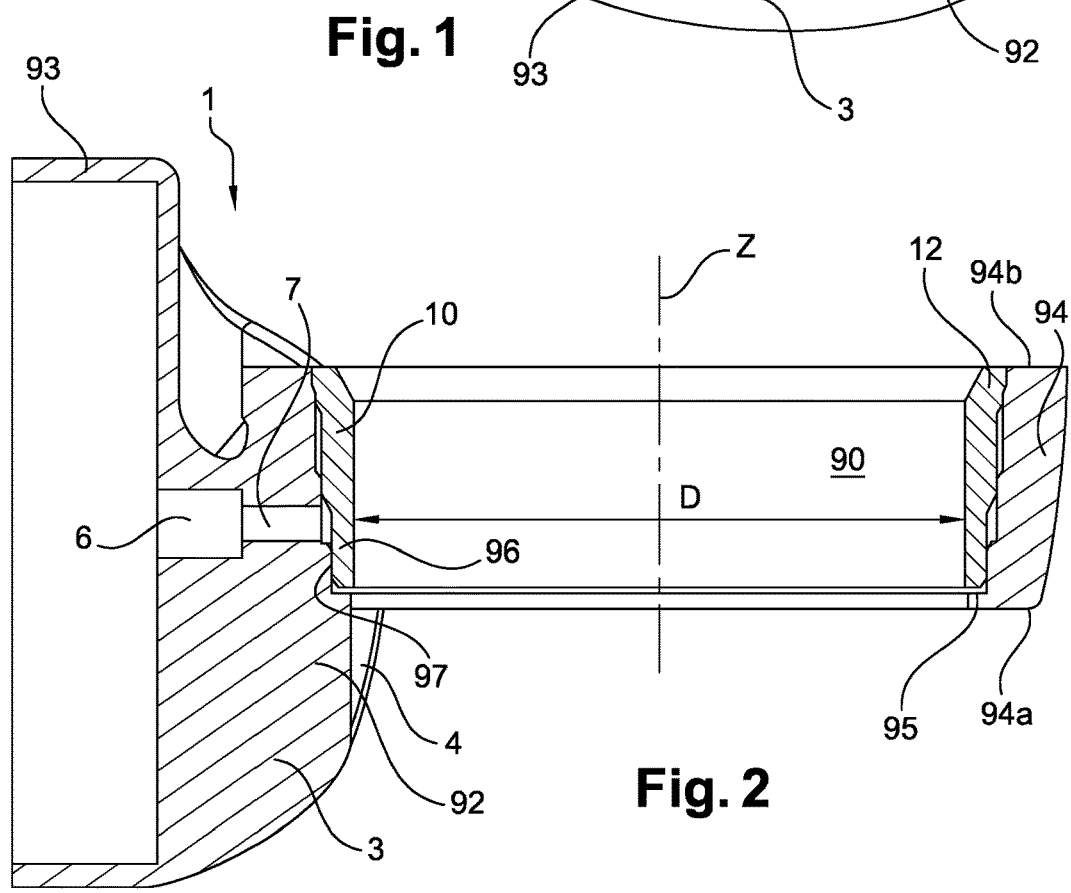
FIG. 2 shows the dispensing means after the engaging part has been fitted in the body.
Figure 3:
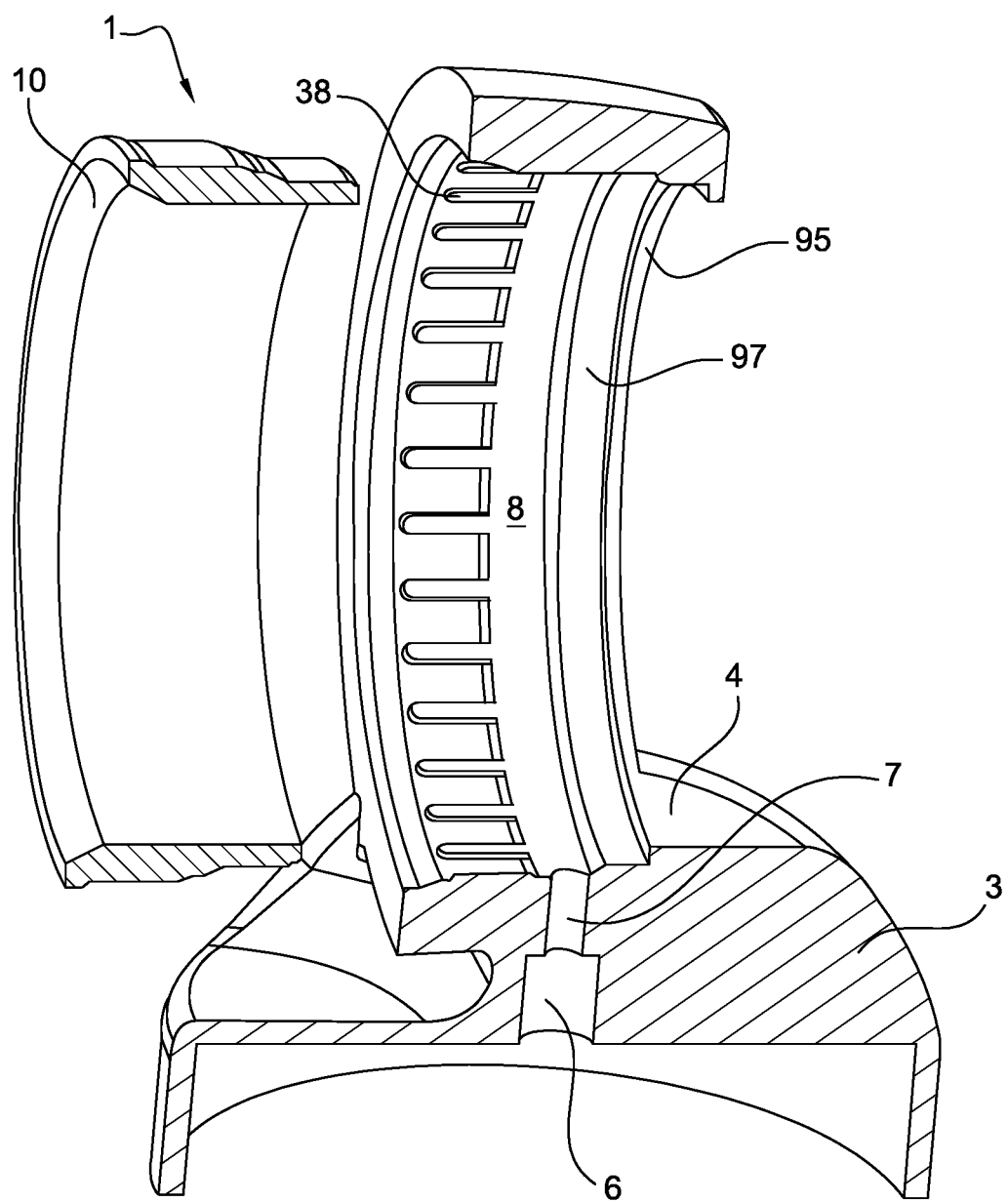
FIG. 3 is a view similar to FIG. 1 in partial section.

The dispensing means 1 shown in FIGS. 1 to 3 is intended to be fitted on a container (not shown) provided with a hollow valve rod or hollow pump rod, through which the product to be dispensed that is contained in the container is conveyed towards the dispensing means 1.

The container may in particular be a pressurized container of the aerosol can type, containing a propellant gas such as compressed air, for example, or a liquefied gas.

The container may be provided with a valve and the valve may be opened for example by pressing the hollow rod or alternatively by tilting the latter. When the container is provided with a pump, the pump may be actuated for example by pressing the hollow rod along its longitudinal axis.

The dispensing means 1 comprises a body 3 which may be produced in an integral manner by moulding a single part or may comprise a plurality of elements produced separately and joined together.

The dispensing means 1 may comprise, as can be seen in FIG. 2, a housing 6 intended to engage with the hollow rod in order to allow the product delivered through the latter to reach a supply duct 7 which opens into a housing 8 in the body 3. The housing 6 has a size adapted to the outside diameter of the rod, so as to obtain a sealed fit of the rod in the housing 6, in order that the product delivered through the rod passes entirely into the supply duct 7. The latter is for example coaxial with the rod of the container but could be oriented in some other way and have for example a plurality of differently oriented portions.

An engaging part 10, called core in the following text when it is inside the body, is fixed in the housing 8 and defines for example with the body 3 a dispensing orifice 12 having an annular cross section, as illustrated.

The expression "annular cross section" should be understood within the meaning of the present invention as meaning any cross section that follows a closed contour, whether this contour is circular, elliptical, polygonal or some other shape.

Passing axially through the core 10 is an opening 90, the inside diameter D of which may be relatively large, for example greater than or equal to 10 mm, better still 15, 20 or 30 mm.

The opening 90 helps to give the dispensing means a particularly aesthetic appearance. In addition, the opening 90 can allow air to flow through the dispensing means under the entrainment effect of a spray emitted through the dispensing orifice 12. This can help to increase the range of the spray and can increase the freshness effect provided thereby, if need be.

The opening 90 may also allow a finger or a lock of hair to be inserted through the dispensing means, and this can make it possible to apply a product in a single movement over the entire circumference of the element inserted through the dispensing means. This can be an advantage for applying for example an antiseptic or care product to a finger or for treating a lock of hair.

The dispensing axis Z may be perpendicular to the longitudinal axis X of the container on which the dispensing means is fitted, as illustrated.

The dispensing means 1 comprises a base 92 which defines a surface 4 on which the user can press in order to bring about dispensing.

The bottom of the base 92 can be extended by an enclosing skirt 93 which covers the upper part of the container.

The housing 8 which receives the core 10 is defined by a crown 94 of axis Z, the lower side of which is joined to the base 92. The supply duct 7 passes through the base 92 and leads into the housing 8 at a distance from the axial ends, along the axis Z, of the crown 94, being preferably closer to the rear end 94a than to the front end 94b, as can be seen in FIG. 2.

The body 3 may have, as illustrated, a shoulder 95 close to the rear end 94a, against which the core 10 can come into axial abutment, if need be, at the end of its fitting.

The core 10 and the housing 8 may have annular surfaces 96 and 97, in sealed contact, in order to close the space formed between the core 10 and the body 3 at the rear of the supply duct 7.

Preferably, the circumferential width I of the dispensing orifice 12, around the spraying direction Z, is constant. If this width I varies, for example so as to take into account the possibly non-uniform pressure drop experienced by the flow of product upstream of the dispensing orifice 12, this does not depart from the scope of the present invention. This non-uniform pressure drop results for example from the geometry of the space between the core and the body, in particular the presence of angles or intersections. By varying the width I, it is possible to ensure that the product can emerge more easily at the point where this pressure drop is greatest, if a spray which is as homogeneous as possible is desired.

The width I of the dispensing orifice is for example between 0.01 and 2 mm.

The core 10 can be fixed to the body 3 in various ways. In the example illustrated in FIGS. 1 to 3, the core 10 is retained on the body 3 by friction.

In the example illustrated, the core 10 is produced separately from the body 3 and is attached to the latter. The core 10 can be produced from the same thermoplastic material as the body 3 or alternatively from a different thermoplastic material. It is also possible to use a metal material to produce the core 10.

Axial ribs 38 are formed on the internal circumference of the housing 8, as can be seen in particular in FIGS. 1 and 3, in order to centre the core 10 in the housing 8. The centring reliefs 38 may be, as illustrated in FIGS. 12A to 12C, parallel or oblique in the circumferential direction with respect to the axis Z, or curved. Each relief 38 may have, when seen in a top view, a contour that is polygonal, in particular rectangular or trapezoidal, or that has a shape that is flared in the direction of the dispensing edge. Two centring reliefs 38 may define, between one another, a narrowing 39 in the vicinity of the dispensing orifice so as to accelerate the fluid via the Venturi effect. The number of centring reliefs 38 is preferably at least 10, better still 20, even better still 40.

The space 22 formed between the core 10 and the body 3 may have the configuration illustrated schematically in FIG. 4A, and open onto the dispensing orifice 12 by way of an annular terminal portion 22c formed between two surfaces 3a and 10a which are in the form of cylinders of revolution about the axis Z.

The terminal wall 22c is attached to a proximal portion 22a by way of an inclined intermediate portion 22b formed between opposite surfaces 3b and 10b.

The centring reliefs 38 extend in the proximal portion 22a. The latter is supplied with product via the dispensing chamber 22d.

When the user actuates the dispensing means 1, the product passes through the supply duct 7 into the space 22 between the core 10 and the body 3 and can be delivered in the form of a spray through the dispensing orifice 12.

In the example in FIGS. 1 to 3, the spray is continuous angularly around the dispensing axis on account of the absence of contact between the core 10 and the body 3 in the region of the dispensing orifice 12. Specifically, the bearing region or regions between the core 10 and the body 3 are for example located, as illustrated, set back from the dispensing orifice 12 by a distance (measured along the dispensing axis Z) of at least 0.5 mm.

The spray may be discontinuous angularly around the dispensing axis on account of the presence, in particular at the reliefs 38, of contact between the core 10 and the body 3 where the product emerges.

Preferably, the cross section of the supply duct 7 is greater than the section of the dispensing orifice 12 so as to allow the space located upstream of the dispensing orifice to be filled rapidly with the product, this being able to help to form a homogeneous spray right from the start of spraying.

The dispensing chamber 22d formed upstream of the space 22a in which the centring reliefs 38 extend receives the product delivered through the supply duct 7.

The width ω of the dispensing chamber 22d is greater than that I of the terminal portion 22c which opens onto the dispensing orifice 12.

The dispensing chamber 22d improves the dispensing of the product before the latter reaches the narrower portions of the passage through which the product is evacuated.

FIGS. 4B and 4C illustrate different other examples of possible configurations for the space 22 formed between the core 10 and the body 3 for the product to flow to the dispensing orifice.

In the example in FIG. 4B, the space 22 formed between the core and the body comprises a proximal portion 22a in which the reliefs 38 for centring the core 10 in relation to the body 3 extend, extended by an intermediate portion 22b which forms an angle with the spraying direction Z, for example a re-entrant angle. This intermediate portion 22b can be attached to a terminal portion 22c, which opens onto the dispensing orifice 12, this terminal portion being defined for example, as illustrated, between two surfaces 3a and 10a, in the form of cylinders of revolution, parallel to the dispensing direction Z. The variant in FIG. 4B does not have a dispensing chamber.

In the variant in FIG. 4C, the terminal portion 22c communicates directly with that portion 22a in which the centring reliefs 38 extend. The terminal portion 22c forms, for example, an angle with the dispensing direction Z. Thus, in axial half section, the axis Z 1 of the orifice 12 is for example convergent, as illustrated.

In the variant in FIG. 4D, the engaging part 10 is outside the body 3. The engaging part 10 is fixed to the body 3 so as to form with the latter the dispensing chamber 22d, facing the supply duct 7. The portions 22a, 22b and 22c allow the product to be conveyed to the dispensing orifice 12.

The supply duct 7 opens for example into the dispensing chamber 22d via a portion oriented parallel to the dispensing axis Z.

Centring reliefs 38 are produced for example on the body 3. The engaging part 10 can be produced, as illustrated, with an annular lip 39 which partially delimits the dispensing chamber 22d and makes it possible to form a narrowing 47 of the section between the chamber 22d and the portion 22a.

FIG. 4E illustrates the possibility of having an angle which is divergent between the axis Z 2, in axial half-section, of the orifice 12 and the dispensing axis.

In the variant in FIG. 4F, the possibility of having no angle between the dispensing axis and the axis Z of the engaging part 10 is illustrated. The supply duct 7 opens for example onto a dispensing chamber 22d. The product is conveyed towards the dispensing orifice 12 via ducts 22 comprising the reliefs 38. The reliefs 38 extend as far as the edge of the dispensing orifice 12 and define a plurality of orifices allowing the product to be delivered in the form of a plurality of jets.

The invention is not limited to a dispensing head comprising only one dispensing orifice 12 produced in accordance with the invention.

By way of example, FIG. 5 illustrates a dispensing head 1 which comprises two dispensing orifices 12.

When there are a plurality of dispensing orifices, these may be distributed in multiple ways on the dispensing means. For example, the spraying axes are parallel, or form an angle, in that, for example, they intersect.

FIGS. 7, 8A and 8B illustrate the possibility for the dispensing means to have a plurality of dispensing orifices 12 formed entirely in the core 10 in order to dispense the product in the form of a plurality of jets for example. The dispensing orifices 12 may have many shapes when observed along their transverse axis, especially being circular or triangular, as illustrated in FIGS. 8A and 8B. The dispensing orifices 12 may be drilled into the core 10, for example by laser drilling.

The core 10 may have a U-shaped axial half-section, as illustrated in FIG. 7. The body 3 may comprise two concentric mounting skirts 41 which define between them a space for mounting the core 10, and may comprise, at its centre, a crown 43 serving to support the engaging part 10. The skirts 41 define, with the crown 43, two annular ducts 45 into which the arms of the U fit. The crown 43 may have, for each orifice 12, two ducts 22 for supplying liquid to this orifice 12.

Figure 14:
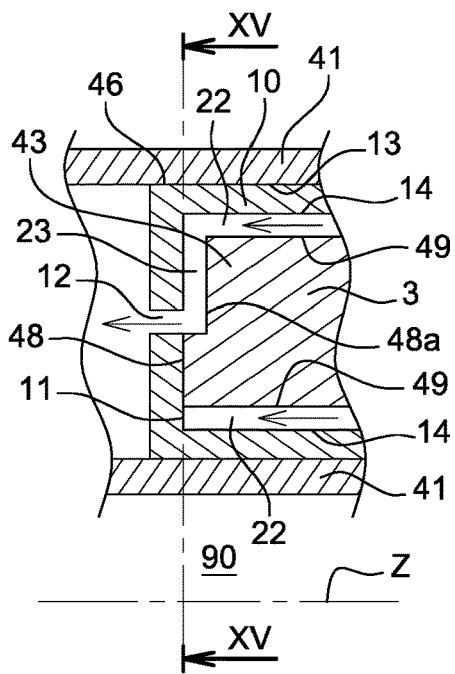
FIG. 14 is a partial axial section through a variant embodiment of the dispensing orifice.
Figure 15:
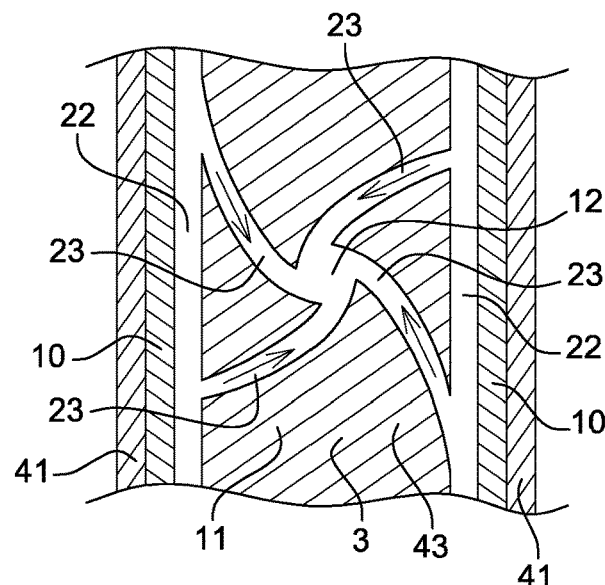
FIG. 15 is a section along XV in FIG. 14.
Figure 16:
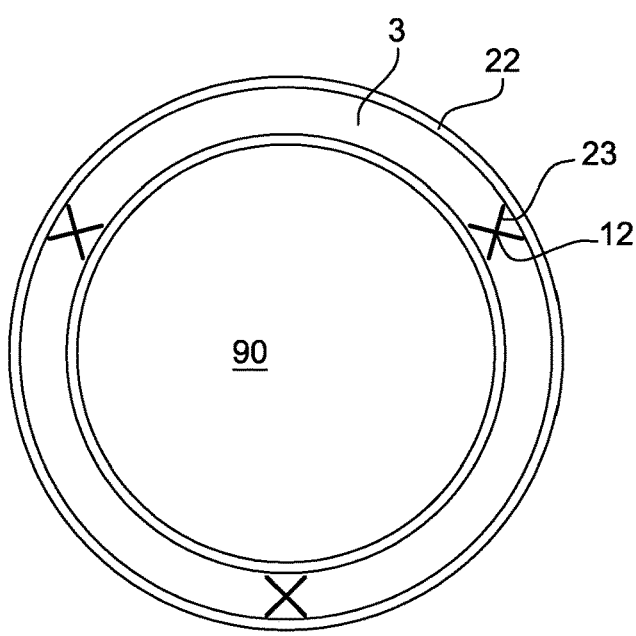
FIG. 16 is an exemplary embodiment of the body according to FIG. 14.
Figure 17:
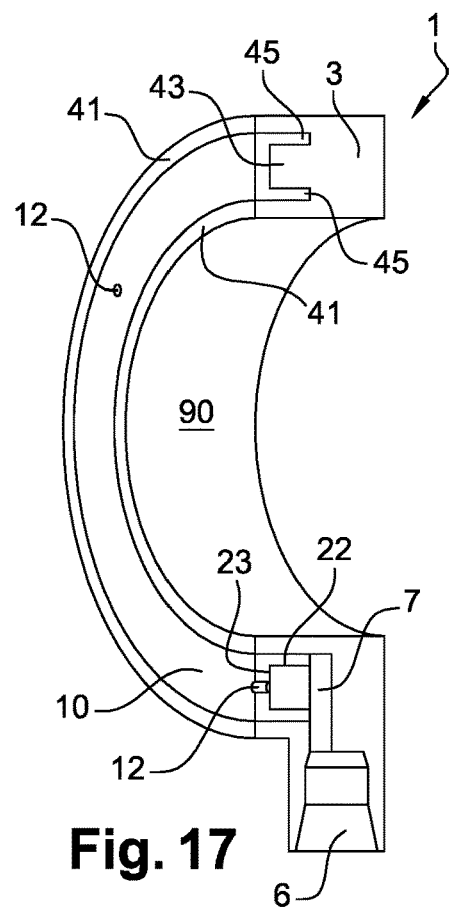
FIG. 17 is a cutaway perspective view of an example of a dispensing means according to the configuration in FIG. 14.

During mounting, as illustrated in FIGS. 14 and 17, the core 10 may bear against the protrusion 43, the end face 48 of the crown 43 being in contact with the internal face 11 of the core 10. The arms of the U of the core 10 are fixed in the ducts 45, the internal face 46 of the mounting skirts 41 being in contact with the face 13 of the core 10. The internal faces 14 of the arms of the U and the lateral surfaces 49 of the crown 43 may define, between one another, the ducts 22 for supplying liquid to the dispensing orifice 12. The crown 43 may have, especially in the form of impressions, on its outer face 48, supply ducts 23 allowing the liquid to pass from the supply ducts 22 to the dispensing orifice 12.

The supply ducts 22 open, upstream of the dispensing orifices 12, onto the supply ducts 23, which lead to the dispensing orifice 12. The supply ducts 23 generate, via their orientation relative to the dispensing orifice, a swirling flow at the outlet of the dispensing orifice 12. This configuration is more particularly useful in the case of a non-liquefied carrier gas.

In one variant, the supply ducts 22 may take the form of impressions on the lateral surface 49 of the body and/or on the internal faces 14 of the core 10.

In one variant (not shown), the core 10 possesses, especially in the form of impressions on its internal face 11, supply ducts 23, the end face 48 of the crown 43 being able to be smooth.

In one variant, the crown 43 is not circumferentially continuous and defines protrusions. The protrusions are placed upstream of the dispensing orifices 12 and may possess, upstream of the dispensing orifices 12, supply ducts 22 and 23 such as described above.

In the variant in FIGS. 4F, 9 and 10, the dispensing orifices 12 are formed between the core 10 and the body 3, being for example distributed all around the spraying axis Z. The core 10 or the body 3 may have centring reliefs 38 that circumferentially bound the dispensing orifices 12. The centring reliefs 38 may, as illustrated in FIGS. 12A to 12C, extend as far as the edge of the core 10 over its entire periphery and define, between one another, dispensing orifices 12. The number of dispensing orifices 12 is preferably at least 10, better still 20, even better still 40. The cross section of a dispensing orifice 12 is for example greater than 0.003 mm$^2$. The dispensing orifices 12 are preferably spaced apart by a space of at least 1 mm, which is the same as the pitch p between the centring reliefs. As illustrated in FIGS. 10A and 10B, the dispensing orifices 12 can have a polygonal cross section, in particular a triangular cross section.

The core 10 may, as illustrated in FIG. 13A, extend set-back relative to the body by an amount between 0.01 and 1 mm, better still between 0.01 and 0.5 mm. The body 3 protrudes into the dispensing orifice and may generate a convergent spray. The core 10 may, as illustrated in FIG. 13B, be flush with the body 3. The spray can then be straight.

The core 10 may extend, as illustrated in FIG. 13C, forwards relative to the body 3 by an amount between 0 and 1 mm, better still between 0 and 0.5 mm. The spray can then be divergent.

If an additional dispensing orifice is provided, for example by attaching inside the core 10 a second core 50 which defines with the first core 10 a second dispensing orifice 51 which is coaxial with the first dispensing orifice, as illustrated in FIG. 6, this does not depart from the scope of the present invention. A passage 90 continues to be formed through the dispensing means.

The dispensing orifice may be supplied with more than one product.

The dispensing means may be supplied with two products which are dispensed through separate dispensing orifices.

It is possible for the axis Z not to be perpendicular to the axis of the rod of the container on which the dispensing means is fitted, as illustrated in FIG. 11. In this example, the axis Z is oriented upward when the container is vertical with the dispensing means at the top.

The supply duct 7 can be oriented substantially parallel to the dispensing axis Z, at least in the case of the portion which opens out facing the engaging part 10. The latter may be produced with an annular lip 39 which defines a narrowing of the section 47.

The configuration may be similar to that in FIG. 4D apart from the fact that the engaging part 10 is outside the body 3 in the example in FIG. 4D and inside it in the example in FIG. 11.

The dispensing means may be arranged so as to allow a protective cap to be fitted and to comprise, if need be, an on/off system that makes it possible to prevent the actuation of the device when the dispensing means is in a certain position with respect to the container or when a locking element of the dispensing means is in a certain position in relation to the latter.

In variants which are not illustrated, the dispensing orifice is formed between a body and an engaging part, the body being radially on the inside with respect to the engaging part, the supply duct for the product passing through the body. All of the features described with reference to the figures can be found in variants in which the body is radially on the inside with respect to the engaging part.

The example that follows serves to illustrate the invention.

EXAMPLE

In the example that follows, all the amounts are indicated as weight percentage of product as active materials relative to the total weight of the composition.

The following composition was prepared from the compounds indicated in the table below.

| | |
|---|---|
| VP/VA Copolymer[1] | 0.01 |
| Mineral oil liquid paraffin[2] | 0.48 |
| Isopropyl palmitate | 4.80 |
| Dimethicone[3] | 4.50 |
| Octyldodecanol[4] | 1.02 |
| Fragrance | 0.21 |
| Butane | 40.00 |
| Ethanol | qs 100 |

[1] sold under the trade name Luviskol VA 64 by BASF
[2] sold under the trade name Marcol 82 by ExxonMobil Chemical
[3] sold under the trade name Element 14 PDMS 10-A by Momentive Performance Materials
[4] sold under the trade name Isofol 20 N/F by Sasol The aerosol device according to the invention, illustrated in FIG. 1, was used to package the compositions above. It comprises the following characteristics:
- a valve equipped with a nozzle with an orifice 0.4 mm in size and an internal restriction orifice 0.3 mm in size,
- a dispensing means comprising 10 orifices having a unit cross section of 0.25 mm, distributed over the annular surface area.

The compositions were sprayed onto a head of hair. A wide and vaporous diffusion is obtained which allows an extremely fine and light deposit, uniformly distributed over the head of hair.

After drying, it is noted that the hair is shiny with a very natural look.

The invention claimed is:

1. A hair treatment process comprising:
    applying to the hair a composition comprising at least one fatty substance using an aerosol device, wherein the aerosol device comprises:
        a container containing the composition and at least one propellant, wherein the at least one propellant possibly is present in the composition or in the container, separate from the composition; and
        a diffuser for dispensing said composition, the diffuser comprising:
            a body extending around a dispensing axis and being open at two opposite axial ends, and
            an engaging part extending around the dispensing axis and being open at two opposite axial ends, wherein the engaging part at least partially defines a dispensing orifice.

2. The process of claim 1, wherein the at least one fatty substance is chosen from $C_6$-$C_{16}$ hydrocarbons, hydrocarbons containing more than 16 carbon atoms, triglycerides, fatty alcohols, esters of fatty acids, esters of fatty alcohols other than triglycerides, silicones, or mixtures thereof.

3. The process of claim 1, wherein the composition comprises a fatty ester and at least one non-silicone oil.

4. The process of claim 1, wherein the at least one fatty substance is liquid at room temperature and at atmospheric pressure.

5. The process of claim 1, wherein the at least one propellant is present in the composition, and the at least one fatty substance is present in an amount ranging from 0.1% to 80% by weight, relative to the total weight of the composition.

6. The process of claim 1, wherein the composition further comprises at least one $C_2$-$C_4$ monoalcohol.

7. The process of claim 6, wherein the at least one $C_2$-$C_4$ monoalcohol includes ethanol.

8. The process of claim 6, wherein the at least one propellant is present in the composition, and the at least one $C_2$-$C_4$ monoalcohol is present in an amount ranging from 1% to 70% by weight, relative to the total weight of the composition.

9. The process of claim 1, wherein the at least one propellant is chosen from air, nitrogen, carbon dioxide, dimethyl ether, $C_3$-$C_5$ alkanes, 1,1-difluoroethane, or mixtures thereof.

10. The process of claim 1, wherein the at least one propellant is present in the composition, and the at least one propellant is present in an amount ranging from 10% to 90% by weight, relative to the total weight of the composition.

11. The process of claim 1, wherein the composition further comprises at least one additive chosen from conditioning or fixing anionic, cationic, nonionic, amphoteric or zwitterionic polymers, fragrances, dyes, protective screening agents, acids, bases, nacres, or glitter flakes.

12. The process of claim 1, wherein the dispensing orifice is defined between the engaging part and the body.

13. The process of claim 1, wherein the dispensing orifice is annular.

14. The process of claim 1 wherein the dispensing orifice has a constant width in the circumferential direction.

15. The process of claim 1, wherein the dispensing orifice has axial symmetry.

16. The process of claim 1, wherein the engaging part at least partially defines a plurality of dispensing orifices.

17. The process of claim 16, wherein the number of dispensing orifices is between 2 and 80.

18. The process of claim 16, wherein the dispensing orifices each have a cross section greater than or equal to 0.0025 $mm^2$.

19. The process of claim 1, wherein applying the composition to the hair is performed to give the hair sheen.

20. An aerosol device comprising:
    a container containing:
        at least one propellant, and
        a composition comprising at least one fatty substance chosen from fatty acid esters or fatty alcohol esters, and at least one non-siliconized oil,
        wherein the propellant is either present in the composition or in the container, separate from the composition; and
    a diffuser for dispensing said composition, the diffuser comprising:
        a body extending around a dispensing axis and being open at two opposite axial ends; and
        an engaging part extending around a dispensing axis and being open at two opposite axial ends, wherein the engaging part at least partially defines a dispensing orifice.

* * * * *